United States Patent [19]

Yahagi et al.

[11] Patent Number: 4,568,766

[45] Date of Patent: Feb. 4, 1986

[54] 4-HYDROXY-4'-ISOPROPOXYDIPHENYL-SULFONE AND ITS USE FOR COLOR-DEVELOPABLE RECORDING MATERIAL

[75] Inventors: Masakichi Yahagi, Tokyo; Tetsuo Igaki, Kawagoe; Shinji Yoshinaka, Iwatsuki; Kosaku Morita, Saitama; Kimiaki Kinoshita, Kitamoto; Masashi Enokiya, Tokyo; Akio Kaneko, Fujimi; Toshiyuki Yamashita, Tokyo, all of Japan

[73] Assignee: Nippon Soda Company Limited, Tokyo, Japan

[21] Appl. No.: 624,253

[22] Filed: Jun. 25, 1984

[30] Foreign Application Priority Data

Jul. 4, 1983 [JP] Japan ................... 58-120209

[51] Int. Cl.$^4$ ........................... C07C 147/00

[52] U.S. Cl. .................... 568/33; 346/216; 346/225; 427/150

[58] Field of Search .......... 346/216, 225, 217; 568/33; 427/150-152

[56] References Cited

U.S. PATENT DOCUMENTS 4,446,209 5/1984 Iwakura et al. ............ 346/216
4,453,744 6/1984 Würmli et al. ............ 346/216

FOREIGN PATENT DOCUMENTS 0020493 2/1983 Japan ........................ 346/216
WO84/02882 8/1984 PCT Int'l Appl. ........... 346/216

*Primary Examiner*—Bruce H. Hess
*Attorney, Agent, or Firm*—George B. Oujevolk

[57] ABSTRACT

4-Hydroxy-4'-isopropoxydiphenylsulfone useful as color developer for heat-sensitive color-developable recording material.

2 Claims, No Drawings

4-HYDROXY-4'-ISOPROPOXYDIPHENYLSULFONE AND ITS USE FOR COLOR-DEVELOPABLE RECORDING MATERIAL

DETAILED EXPLANATION OF THE INVENTION

Background of the Invention

This invention relates to a novel compound of 4-hydroxy-4'-isopropoxydiphenylsulfone having a formula of

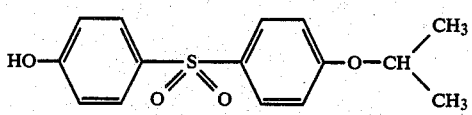

and more particularly to a heat-sensitive color-developable recording material that contains colorless or light-colored, color-developing dye that develops a color by the action of acidic substance, and 4-hydroxy-4'-isopropoxydiphenylsulfone as color developer.

In general, in the heat-sensitive recording system using a colorless or light-colored, color-developing dye that develops a color by the action of acidic substance (hereunder referred to as "color developing dye"), the color developing dye is allowed to develop a color, under heat, by the action of acidic substance (color developer). Facsimile or other recording devices for communications, in which this heat-sensitive recording system is used, have come to have increasingly high operating speeds. And with this, demands are strong for the increased color developing velocity or for the improved color developing property at low temperature (higher coloring sensitivity) of recording paper. Recently however, demand for longer storage-life of the recording paper becomes greater, and its high resistance to light or to high-temperature and high-humidity condition, before and after color developing, is strongly required.

Also high in demand is the improved resistance of the color-developed areas of recording paper to the grease or to the sweat on the fingers (that may contact them in handling the paper).

In addition, it is necessary to prevent what is called "blooming" in which white fine powders emerge locally or generally on color-developing areas with the passage of time. (Blooming is also known as "whitening" and is considered as a result of the liberation and precipitation of the developer used to the heat-sensitive mixture composition that is applied on the surfaces of the recording paper.)

Further still, the whiteness of the heat-sensitive recording paper is one of the major factors that determine its market value. For this reason, fouling on the paper surface must be reduced to the minimum.

As color developers of heat-sensitive recording material whose chemical structures are similar to that of the 4-hydroxy-4'-isopropoxydiphenylsulfone of this invention, 4-hydroxy-4'-methoxydiphenylsulfone and 4-hydroxy-4'-ethoxydiphenylsulfone are shown in the Japanese Patent Publication No. Tokkaisho 57-210886 (1982) and 4-hydroxy-4'-n-butoxydiphenylsulfone is shown in the Japanese Patent Publication No. Tokkaisho 58-20493 (1983). Also 4-hydroxy-4'-n-octyloxydiphenylsulfone and of 4-hydroxy-4'-n-dodecyloxydiphenylsulfone are shown in examples of the Japanese Patent Publication No. Tokkaisho 58-82788 (1983). These known diphenylsulfones have fatal defects as a color developer of heat-sensitive recording material.

SUMMARY OF THE INVENTION

Compared with these known diphenylsulfones, 4-hydroxy-4'-isopropoxydiphenylsulfone of this invention is obviously excelling as a color developer for heat-sensitive recording material, as described hereafter in detail.

Accordingly, it is an object of this invention to provide a heat-sensitive color-developable recording material, particularly heat-sensitive recording sheet and paper, which is generally remarkable satisfactory on all points described hereafter.

It is another object of this invention to provide a heat-sensitive color-developable recording material, which has higher coloring sensitivity.

It is another object of this invention to provide a heat-sensitive color-developable recording material, which has the superior light-resistance.

It is another object of this invention to provide a heat-sensitive color-developable recording material, which has superior stability of color at storage in an environment of high temperature and high humidity.

It is another object of this invention to provide a heat-sensitive color-developable recording material, its developed color has good resistance to grease or sweat on handling fingers.

It is another object of this invention to provide a heat-sensitive color recording material, which is free from "blooming".

It is another object of this invention to provide a heat-sensitive color recording material, which has high grade of whiteness on the surface.

It is another object of this invention to provide a novel compound of 4-hydroxy-4'-isopropoxydiphenylsulfone and method for preparation thereof.

Other and further objects, features and advantages of the invention will appear more fully from the following description. This invention relates to a novel compound of 4-hydroxy-4'-isopropoxydiphenylsulfone having a formula of

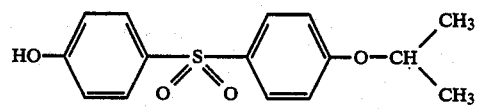

and a heat-sensitive color-developable recording material which is characterized in containing colorless or light-colored, color-developable dye that develops a color under the action of acidic substance, and in containing 4-hydroxy-4'-isopropoxydiphenylsulfone as a developer.

DETAILED DESCRIPTION

A novel compound of 4-hydroxy-4'-isopropoxydiphenylsulfone of this invention is used as a color developer for heat-sensitive color developable recording material (including heat-sensitive recording paper and electro-thermosensitive recording paper but not at all being limited to them) in the same method as in one in which popular developers are used for heat-sensitive recording material. To specify, similar to other developers for heat-sensitive recording paper, 4-hydroxy-4'-isopropoxydiphenylsulfone of this invention is used in a ratio of 0.1~10 parts, preferable 1.5~4.5 parts, to 1 part of a color-developing dye. Fine particles of this compound are dispersed in an aqueous solution of a water soluble binder together with fine particles of a color-developing dye and a filler and, as needed, together with fine particles of a sensitizer. The aqueous suspension so obtained (coating suspension) is then applied, by such method of roll coating on a surface of paper or other suitable sheet substrate and subsequently dried to produce heat-sensitive recording materials. On the surface of the sheet substrate, a layer of the mixture containing fine particles of color-developing dye and the color developer of this invention is formed.

For color developing dyes, various types of dye such as fluoran, phthalide, lactam, triphenylmethane, spiropyran and other types of leuco dyes can be used, but usable dyes are not limited to these only. Besides, these color developing dyes can be mixed in different combinations.

For sensitizers, various kinds of sensitizer can be used e.g., dibenzyl terephthalate (DBT), dibenzyl isophthalate (DBI), bis(tertiary butylphenol)-series compounds or high fatty acid amide, etc. which are known to the technological field concerning can be used. DBT and DBI are here used respectively in a ratio of 0.5~6.0 parts to 1 part of color developing dye. In the case of DBT, DBT is employed in a ratio of 0.5~6.0, preperably, 0.5~4.0 parts to 1 part of color developing dye and in the case of DBI, DBI is employed in a range of 0.3~4.0, preferably, 0.3~3.0 parts to 1 part of the dye. If the amount of their use is too small, their effects as sensitizer become insufficients, whilst if the amount used is excessive, the effect does not become larger in proportion to increase of the amount and it becomes less economical. Particularly when DBT or DBI is used with 4-hydroxy-4'-isopropoxydiphenylsulfone of this invention, the color developing temperature is lowered and whiteness of the recording paper surface is remarkably improved.

As water-soluble binders, various kind of popular binders for example, polyvinylalcohol, hydroxyethylcellulose, carboxymethylcellulose, salt of copolymer of styrene-maleic anhydride, styrene-butadiene copolymer emulsion, vinyl acetate-maleic anhydride emulsion, polyacrylate, polyacrylamide, starches, casein, and gum arabic can be employed, but this listing does not give any limitation.

As fillers, there are, for example, clay, talc, kaolin, satinwhite, titanium oxide, calcium carbonate, magnesium carbonate, barium sulfate, magnesium silicate, aluminium silicate, etc.

The suspension can further contain dispersants (e.g., sodium dloctylsuccinate, sodium dodecylbenzenesulfonate, sodium salts of laurylalcohol sulfuric ester, metallic salts of fatty acid, etc.), desensitizers (e.g., aliphatic higher alcohol, solid polyhydric alcohol, polyethylene, glycol, guanidine derivatives, etc.), antitac agents (e.g., stearic acid, zinc stearate, calcium stearate, carnauba wax, paraffin wax, ester wax, etc.), antifoaming agents, light stabilizers and fluorescent brightening agents.

The suspension is not only used for a heat-sensitive recording material. When the suspension is applied on the conductive layer on a substrate as specified in the Japanese Patent Publication No. Tokkosho 51-16154 (1976) or No. Tokkosho 51-16155 (1976), then it provides electro-thermosensitive recording material.

A novel compound of this invention, 4-hydroxy-4'-isopropoxydiphenylsulfone can be synthesized by reacting bis(p-hydroxyphenyl)sulfone with isopropylhalogenide such as isopropylbromide and isopropyliodide in the presence of organic solvent and acid-binding agent at a temperature of 50°~200° C. for 1~5 hours, and 4-hydroxy-4'-isopropoxydiphenylsulfone has the melting point of 129.0°~131.0° C.

The function of the developer of this invention is the same as one of popular developer. Namely, when the part to be color developed on the recording material is heated to approximately 80°~250° C., the developer of this invention becomes soft, fused or melted, and then the color developes on the part by intimately contacting of the color-developable dye and the developer of this invention.

Advantages of this invention are explained in detail with compered with similar known sulfones.

When similar known 4-hydroxy-4'-n-octyloxydiphenylsulfone and 4-hydroxy-4'-n-dodecyloxydiphenylsulfone were used for preparation of coating suspension for heat-sensitive recording paper in a same method as specified in Example 1 of this invention, the coating suspension already colored grey at the stages of its preparation and made it impossible to produce therefrom heat-sensitive recording paper with white surfaces.

Similar to this, when a coating suspension containing 4-hydroxy-4'-methoxydiphenylsulfone was applied on a surface of recording paper, the surface conspicuously turned grey at a stage of drying the paper and it became apparent that 4-hydroxy-4'-methoxydiphenylsulfone is far from usable as a developer for heat-sensitive recording paper.

Different heat-sensitive recording papers were produced using, as their color developing dyes, 3-N-methyl-cyclohexylamino-6-methyl-7-phenylaminofluoran, 3-diethylamino-6-methyl-7-phenylaminofluoran, and CVL (Crystal Violet Lactone), and by also using, as developers, 4-hydroxy-4'-isopropoxydiphenylsulfone (compound A) of this invention, 4-hydroxy-4'-ethoxydiphenylsulfone (compound B), 4-hydroxy-4'-n-butoxydiphenylsulfone (compound C), and 2,2-bis(p-hydroxyphenol)propane (bisphenol A) which is currently the most popularly used as a color developer for heat-sensitive recording paper. These heat-sensitive recording papers were then compared by measuring whiteness of the paper surface before color-developing and the color density after color developing using Macbeth reflection densitometer. In the tables, smaller values of whiteness of paper surface indicate higher whiteness, and larger values of color density indicate denser coloration. The results are listed in Table 1 to Table 3.

The methods in which these heat-sensitive recording papers were produced, the methods in which color were developed and in which the surface whiteness and the color density were measured, are described in the Examples and Comparative Examples of this invention:

TABLE 1

Color developing dye: 3-N—methyl-cyclohexylamino-6-methyl-7-phenylaminofluoran (black color developing dye)

| Heat-sensitive recording paper No. | Developer compound | Whiteness of Paper surface | Color density Color developing temperature (°C.) | | | | | | |
|---|---|---|---|---|---|---|---|---|---|
| | | | 85 | 90 | 95 | 100 | 110 | 120 | 150 |
| I | A (this invention) | 0.10 | 0.17 | 0.37 | 0.80 | 1.15 | 1.21 | 1.21 | 1.24 |
| II | B (comparison) | 0.18 | 0.19 | 0.21 | 0.23 | 0.29 | 0.57 | 0.87 | 1.23 |
| III | C (comparison) | 0.11 | 0.56 | 0.83 | 0.97 | 0.99 | 1.01 | 1.03 | 1.11 |
| IV | bisphenol A (comparison) | 0.12 | 0.17 | 0.24 | 0.41 | 0.71 | 1.12 | 1.16 | 1.22 |

(Note) In measurement, the Wratten filter No. 106 was used.

TABLE 2

Color developing dye: 3-diethylamino-6-methyl-7-phenylaminofluoran (black color developing dye)

| Heat-sensitive recording paper No. | Developer compound | Whiteness of Paper surface | Color density Color developing temperature (°C.) | | | | | | |
|---|---|---|---|---|---|---|---|---|---|
| | | | 85 | 90 | 95 | 100 | 110 | 120 | 150 |
| V | A (this invention) | 0.09 | 0.14 | 0.43 | 0.90 | 1.22 | 1.22 | 1.23 | 1.26 |
| VI | B (comparison) | 0.19 | 0.20 | 0.21 | 0.23 | 0.29 | 0.57 | 0.82 | 1.24 |
| VII | C (comparison) | 0.11 | 0.58 | 0.82 | 0.87 | 1.00 | 1.01 | 1.03 | 1.09 |
| VIII | bisphenol A (comparison) | 0.11 | 0.12 | 0.17 | 0.27 | 0.69 | 1.13 | 1.16 | 1.21 |

(Note) In measurement, the Wratten filter No. 106 was used.

TABLE 3

Color developing dye: Crystal Violet Lactone (blue color developing dye)

| Heat-sensitive recording paper No. | Developer Compound | Whiteness of Paper surface | Color density Color developing temperature (°C.) | | | | | | |
|---|---|---|---|---|---|---|---|---|---|
| | | | 85 | 90 | 95 | 100 | 110 | 120 | 150 |
| IX | A (this invention) | 0.08 | 0.12 | 0.50 | 0.96 | 1.22 | 1.22 | 1.22 | 1.22 |
| X | B (comparison) | 0.09 | 0.10 | 0.10 | 0.12 | 0.14 | 0.55 | 0.90 | 1.19 |
| XI | C (comparison) | 0.08 | 0.62 | 0.94 | 1.00 | 1.00 | 0.97 | 0.96 | 0.98 |
| XII | bisphenol A (comparison) | 0.10 | 0.20 | 0.48 | 0.83 | 1.11 | 1.23 | 1.23 | 1.23 |

(Note) In the measurement of paper surfaces, the Wratten filter No. 106 was used, whereas in that of color density, the Wratten filter No. 25 was employed.

These test results show that the heat-sensitive recording paper II, where compound B is used, has a conspicuously foul surface and has low sensitivity for color developing. The compound B, therefore, is wholly unsatisfactory as a developer for heat-sensitive recording paper. When compound A (this invention) and Compound C are comparatively studied, it is found that, in the whiteness of the surface, the heat-sensitive recording paper I in which compound A is used is obviously superior to the heat-sensitive recording paper III, in which compound C is employed. In a temperature range of up to 100° C. or thereabouts, heat-sensitive recording paper III excels heat-sensitive recording paper I in the color density.

In a range above 100° C., however, heat-sensitive recording paper I is superior to the recording paper III in color density, and at the color developing temperature of 150° C., where color density is considered to attain saturation, a marked difference is found between the values of color density of these recording papers. Definitely, this difference relates with color fastness properties of these color-developing dyes under various conditions.

Recording paper IV in which bisphenol A is used as developer, is significantly inferior to recording paper I both in the whiteness of the paper surface and in color-developing sensitivity.

The results of the color fastness test on these heat-sensitive recording papers are described below.

In the color fastness tests on recording paper I to VIII, the papers on which a color had not yet developed (non-color-developed papers) were subjected to "constant temperature and constant humidity test", which test keeps the recording paper for 24 hours in an environment controlled at a temperature of 50° C. and relative humidity of 80%, and to "light-resistance test", which test exposes the coated surface of the recording paper to sunbeams for 10 hours. In these tests, paper surface was examined for a change in the degree of whiteness. By contrast, the fastness tests of developed color were carried out by using color developed papers, which had been developed at 150° C., under the same test conditions as the above to examine a change of their color density.

The test results of color density are shown in Table 4 and Table 5. When tested for light-resistance, the surfaces of the non-color-developed paper turned light-yellowish pink, for which reason, the Wratten filter No. 47 was used in measurement. In measurements other than these, the Wratten filter No. 106 was used.

Particularly interesting in other respects is the fact that as compared to 4-hydroxy-4'-isopropoxydiphenylsulfone of this invention, 4-hydroxy-4'-n-propoxydiphenylsulfone (compound D), which is an isomer of the former, is excessively low in color development sensitivity. Table 6 shows this comparison based on the results of the test conducted on the same test conditions as those for the comparative test in Table 1.

TABLE 6

| Heat-sensitive recording paper No. | Developer compound | Whiteness of Paper surface | Color density Color developing temperature (°C.) | | | | | | |
|---|---|---|---|---|---|---|---|---|---|
| | | | 85 | 90 | 95 | 100 | 110 | 120 | 150 |
| I | A (this invention) | 0.10 | 0.17 | 0.37 | 0.80 | 1.15 | 1.21 | 1.21 | 1.24 |
| IX | D (comparison) | 0.10 | 0.11 | 0.13 | 0.15 | 0.20 | 0.64 | 0.74 | 1.19 |

Moreover, the color-developed areas of the heat-sensitive recording paper produced by using compound D are exceedingly low-resistant to cosmetic cream or to stains on finger tips.

TABLE 4

| Heat-sensitive recording Paper No. | Developer compound | Non-color-developed paper | | | Color-developed paper | | |
|---|---|---|---|---|---|---|---|
| | | Before test | After constant temperature /constant humidity test | After light-resistance test* | Before test | After constant temperature /constant humidity test | After light-resistance test |
| I | A (this invention) | 0.10 | 0.12 | 0.23 | 1.24 | 1.20 | 1.21 |
| II | B (comparison) | 0.18 | 0.19 | 0.27 | 1.25 | 1.15 | 1.22 |
| III | C (comparison) | 0.11 | 0.14 | 0.23 | 1.11 | 1.10 | 1.02 |
| IV | bisphenol A (comparison) | 0.12 | 0.17 | 0.23 | 1.22 | 1.15 | 1.20 |

TABLE 5

| Heat-sensitive recording Paper No. | Developer compound* | Non-color-developed paper | | | Color-developed paper | | |
|---|---|---|---|---|---|---|---|
| | | Before test | After constant temperature /constant humidity test | After light-resistance test* | Before test | After constant temperature /constant humidity test | After light-resistance test |
| V | A (this invention) | 0.09 | 0.11 | 0.21 | 1.26 | 1.22 | 1.23 |
| VI | B (comparison) | 0.19 | 0.18 | 0.27 | 1.24 | 1.21 | 1.25 |
| VII | C (comparison) | 0.11 | 0.13 | 0.21 | 1.09 | 1.12 | 1.02 |
| VIII | bisphenol A (comparison) | 0.11 | 0.17 | 0.20 | 1.21 | 1.22 | 1.20 |

These color fastness test results show that on all points, compound A excels compound B, compound C and bisphenol A. In addition to the above-described fastness, the color that develops in heat-sensitive recording papers I and V is obviously most resistant to cosmetic cream and to finger tip stain than the color that develops in heat-sensitive recording papers II, III, IV, VI, VII and VIII.

Currently, benzyl p-hydroxybenzoate is second only to bisphenol A in the quantity used as color developer for heat-sensitive recording paper. The most serious defect of this compound, however, is the occurrence of marked "blooming phenomena". Contrarily, 4-hydroxy-4'-isopropoxydiphenylsulfone of this invention is completely free from "blooming phenomena".

As Table 1 shows, 4-hydroxy-4'-isopropoxydiphenylsulfone of this invention exhibits excellent color developing property at a temperature near or exceeding 100° C. If in combination with this color developer a sensitizer is used, particularly dibenzyl terephthalate (DBT) or dibenzyl isophthalate (DBI), the color developing property of the developer at low temperature can be significantly increased as shown in Table 7. This Table 7 shows the values obtained from the measurements of the heat-sensitive recording paper produced in Example 4 of this invention. Compositions of coating suspensions prepared in Example 4 were composed by substituting a portion of clay used for heat-sensitive recording paper I in Table 1 with the same amount of DBT or DBI.

TABLE 7

| Heat-sensitive recording paper No. | Developer compound | Sensitizer | Whiteness of Paper surface | Color density Color developing temperature (°C.) | | | | | | |
|---|---|---|---|---|---|---|---|---|---|---|
| | | | | 80 | 85 | 90 | 95 | 100 | 110 | 120 |
| XIII | A (this invention) | DBT | 0.09 | 0.90 | 1.00 | 1.07 | 1.19 | 1.22 | 1.24 | 1.25 |
| XIV | A (this invention) | DBI | 0.10 | 0.93 | 1.04 | 1.09 | 1.15 | 1.19 | 1.21 | 1.23 |

To further illustrate this invention, and not by way of limitation, following examples are given.

EXAMPLE 1

Preparation of Heat-sensitive Recording Paper 10.5 g of 4-hydroxy-4'-isopropoxydiphenylsulfone, 41.5 g of aqueous solution of 15% polyvinyl alcohol ("Kuraray-105"; saponification degree: 98.5±0.5 mol%, viscosity: 5.6±0.4 CPS at 4%, 20° C., made by Kuraray Co., Ltd.), 8.0 g of inorganic filler (clay) ("UW-90," Engelhard Inc. U.S.A.) and 40.0 g of pure water were added, together with 150 g of glass beads (1~1.5 mm in diameter), into a 250 ml polyhethylene bottle, which was then stoppered and mounted on a paint conditioner made by Read Devil Co., Ltd.

The mounted bottle was next shaken for 8 hours at an oscillation frequency of 630 times/minute and then the glass beads were removed and an aqueous suspension of 4-hydroxy-4'-isopropoxydiphenylsulfone with grain sizes of 2~3μ was obtained (liquid A).

On the other hand, 7.0 g of 3-N-methyl-cyclohexylamino-6-methyl-7-phenylaminofluoran, 41.5 g of aqueous solution of 15% polyvinyl alcohol (the same as the one specified above), 11.5 g of an inorganic filler (clay) (the same as the above-specified), and 40.0 g of pure water were added, together with 150 g of glass beads, into a 250 ml polyethylene bottle. After it was stoppered, the bottle was shaken for 5 hours at an oscillation frequency of 630 times/minute on a paint conditioner. With the removal of the glass beads, an aqueous suspension of fluoran compounds (particle size: 2~3μ) was obtained (liquid B). Further, 41.5 g of aqueous aolution of 15% polyvinyl alcohol (the same as the above-specified), 18.5 g of an inorganic filler (clay) (the same as the above-specified), and 40.0 g of pure water were introduced, together with 150 g of glass beads, into a 200 ml polyethylene bottle. When the process just described was followed, an aqueous suspension of an inorganic filler was obtained (liquid C). 10 g of liquid A, and 5 g each of liquids B and C were mixed and when the mixture was stirred for 20 minutes, a coating suspension was produced.

This coating suspension was coated onto a white paper by means of Wire Rod No. 12. The drying of the coated paper in hot air stream of 60° C. for 2 minutes produced heat-sensitive recording paper.

Using Dry Heating Tester (made by Kishino Science Machinary Co., Ltd.), this heat-sensitive recording paper was heated on the two sides for 5 seconds at 85° C., 90° C., 95° C., 100° C., 110° C., 120° C. and 150° C. to attain color development (black). The color density (color strength) of the color-developed paper and the whiteness of the surface of non-color-developed paper were measured by Macbeth reflection densitometer RD-514. Table 1 (in the column on heat-sensitive recording paper I) shows the measurement results.

Of the sheets of heat-sensitive recording paper thus measured, non-color developed ones and the ones in which color developed at 150° C. were subjected to a constant temperature/constant humidity test, in which the papers were left to stand for 24 hours in an environment having a temperature of 50° C. and a relative humidity of 80%. They were also irradiated for 10 hours with sunbeams in a test to determine their light resistance. Table 4 (in the column on heat-sensitive recording paper I) shows their whiteness and color density measured after the test.

EXAMPLE 2

Preparation of Heat-sensitive Recording Paper

Instead of the 3-N-methyl-cyclohexylamino-6-methyl-7-phenylaminofluran used as a coloring developing dye in Example 1, 3-diethylamino-6-methyl-7-phenylaminofluoran was used and Example 1 was repeated to produce heat-sensitive recording paper. This heat-sensitive recording paper was then caused to develop a color (black) in the same method as Example I. The whiteness of the paper before the color developed and the color density of the paper after the color developed were measured in the same method as Example 1. Non-color developed paper and color-developed paper were also tested in the same procedures as in Example 1.

Tables 2 and 5 (both in the column on heat-sensitive recording paper V) show the measured values of the specimens.

EXAMPLE 3

Preparation of Heat-sensitive Recording Paper

For a color developing dye, Crystal Violet Lactone was used and a heat-sensitive recording paper is produced in the same method as Example 1. The heat-sensitive recording paper was allowed to develop a color (blue) in the same process as in Example 1. After this, non-color-developed paper was measured for its whiteness of the surface, and the color-developed paper, for its color density. Table 3 (in the column on heat-sensitive recording paper IX) shows the measured values.

COMPARATIVE EXAMPLE 1

As a developer, 4-hydroxy-4'-ethoxydiphenylsulfone (compound B), 4-hydroxy-4'-n-butoxydiphenylsulfone (coumound C), and bisphenol A were individually substituted for the 4-hydroxy-4'-isopropoxydiphenyl sulfone (compound A) used in Example 1, and Example 1 was repeated and heat-sensitive recording papers were produced. When compound C was used, its aqueous suspension gelled, so the suspension was diluted with water and then the glass beads were removed. (The concentration of the coating suspension was made uniform with other cases using a thickened inorganic filler suspension.) By applying these coating suspensions onto a white paper and followed brying, heat-sensitive recording papers (heat-sensitive recording papers II, III, and IV, respectively) were made, which were then allowed to develop colors in the method specified in Example 1.

The whiteness of the papers before the color developed was measured and so was the color density after the color development. Table 1 shows the measured values. Before and after their color developing, these heat-sensitive recording papers were also tested for color fastness in the methods indentical with Example 1. Table 4 shows the measured values.

COMPARATIVE EXAMPLE 2

As a developer, compound B, compound C, and bisphenol A were individually substituted for 4-cydroxy-4'-isopropoxydiphenylsulfone (Compound A) in Example 2, and Example 2 were repeated and a heat-sensitive recording papers were produced. Also in the same method as Example 2, these heat-sensitive recording papers (heat-sensitive recording papers VI, VII and VIII, respectively) were caused to form a color, and measurements were then taken of the whiteness of the non-color-developed papers and of the color density of the papers where thecolor developed. Table 2 shows the measured values.

Before and after their color developing, heat-sensitive recording papers were also put to color fastness test in the same procedures as Example 2. The test results are given in Table 5.

COMPARATIVE EXAMPLE 3

As a developer, the 4-hydroxy-4'-isopropoxydiphenylsulfone (compound A) used in Example 3 was replaced by compound B, compound C and bisphenol A, and in the same method as Example 3, heat-sensitive recording papers were produced. These heat-sensitive recording papers (heat-sensitive recording papers X, XI, and XIII, respectively) were induced to develop a color in the same procedures as Example 3 and the whiteness of the non-color-developed surface and the color density of color-developed paper were measured. Table 3 shows the measured values.

These color-developed papers were smeared with cosmetic cream and finger tip stain. On observation 7 days later, the smeared portions of a color-developed paper, in which compound C (4-hydroxy-4'-n-butoxydiphenylsulfone) was used, were found to have become considerable less dense in color. Contrastingly, the color-developed paper in which compound A (4-hydroxy-4'-isopropoxydiphenylsulfone) was used was found to be practically free from this phenomenon.

EXAMPLE 4

Preparation of Heat-sensitive Recording Paper 7.0 g of dibenzyl terephthalate (DBT), 41.5 g of water solution of 15% polyvinyl alcohol (the same as Example 1), 11.5 g of inorganic filler (the same as example 1), and 40.0 g of pure water were added, together with 150 g of glass beads, into a 250 ml polyethylene bottle, which on being stoppered was shaken for 5 hours at an oscillation frequency of 630 times/minute on a paint conditioner. After this the glass beams were removed, an aqueous suspension of DBT was obtained (liquid D).

By the similantenious method, an aqueous suspension of debenzyl isophthalate (DBI) was obtained (liquid E).

5.0 g of this liquid D was mixed with 10.0 g of the liquid A and 5.0 g of the liquid B used in Example 1 and the mixture was stirred for 20 minutes to prepare a coating suspension. The liquid for application was then used to make a heat-sensitive recording paper (heat-sensitive recording paper XIII) in the same method as Example 1. Then the paper surfaces were measured for whiteness and so was the color density at different temperatures.

Table 7 shows the measured values.

In addition, liquid E was substituted for liquid D and in the above-specified procedures, heat-sensitive recording paper XIV was produced. Table 7 shows the whiteness of the paper surface before the color developed and the color density after the color developed.

EXAMPLE 5

Preparation of 4-hydroxy-4'-isopropoxydiphenylsulfone 30.3 g of bis(p-hydroxyphenyl)sulfone, 18.5 g of isopropylbromide, and 22.2 g of potassium carbonate as acid-binding agent were added to 200 ml of dimethylformamide, then stirred for 4 hours at about 120° C. and dimethylformamide was distilled off under reduced pressure. When this was accomplished, chloroform was added to the residue to extract crude 4-hydroxy-4'-isopropoxydiphenylsulfone. Then this crude compound was refined by using a silica gel column chromatography and 15.7 g of 4-hydroxy-4'-isopropoxydiphenylsulfone was obtained in white microfine crystals with a melting point of 129.0°~131.0° C.

We claim:

1. 4-Hydroxy-4'-isopropoxydiphenylsulfone

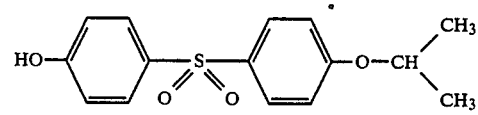

2. A method for the poduction of 4-hydroxy-4'-isopropoxydiphenylsulfone, which comprises reacting bis(p-hydroxyphenyl)sulfone with isopropylhalide.

* * * * *

UNITED STATES PATENT AND TRADEMARK OFFICE
CERTIFICATE OF CORRECTION

PATENT NO. : 4,568,766
DATED : February 4, 1986
INVENTOR(S) : Masakichi Yahagi et al.

It is certified that error appears in the above-identified patent and that said Letters Patent is hereby corrected as shown below:

On the title page Item /73/ should read

-- /73/ Assignee: Shin Nisso Kako Co., Ltd., Tokyo, Japan --.

Signed and Sealed this

Twenty-seventh Day of May 1986

[SEAL]

Attest:

DONALD J. QUIGG

Attesting Officer

Commissioner of Patents and Trademarks